United States Patent [19]

Matthews

[11] 4,409,227

[45] Oct. 11, 1983

[54] 4-(((HETEROCYCLO)THIO)METHYL)BENZOIC ACIDS, ESTERS AND AMIDES AND THEIR PHARMACEUTICAL USE

[75] Inventor: Donald P. Matthews, Indianapolis, Ind.

[73] Assignee: The Dow Chemical Co., Midland, Mich.

[21] Appl. No.: 355,788

[22] Filed: Mar. 9, 1982

Related U.S. Application Data

[62] Division of Ser. No. 65,390, Aug. 9, 1979, Pat. No. 4,325,959.

[51] Int. Cl.$^3$ .................... A61K 31/44; C07D 213/70
[52] U.S. Cl. .................... 424/263; 424/269; 424/275; 546/291; 546/296; 546/301; 546/302; 546/337; 546/342; 548/143; 548/144; 549/65; 549/66; 549/77; 549/79
[58] Field of Search ............... 546/291, 296, 301, 302, 546/337, 342; 424/263, 269, 275; 548/143, 144; 549/65, 66, 77, 79

[56] References Cited

U.S. PATENT DOCUMENTS

| | | | |
|---|---|---|---|
| 1,583,762 | 5/1926 | Sebrell | 548/129 |
| 2,744,908 | 5/1956 | Young | 548/129 |
| 3,895,032 | 7/1975 | Carney | 424/274 |
| 3,941,804 | 3/1976 | Ilvespaa et al. | 424/249 |
| 3,983,164 | 9/1976 | Thorne et al. | 424/308 |
| 3,992,386 | 11/1976 | Schact et al. | 424/258 |
| 4,097,669 | 6/1978 | Reisdorff et al. | 542/413 |
| 4,117,158 | 9/1978 | Shepherd | 424/304 |

FOREIGN PATENT DOCUMENTS 1437781 6/1976 United Kingdom .

OTHER PUBLICATIONS

Chem. Abstr. 52: 10777e, (1958).
Chem. Abstr. 73: 45516w, (1970).
Chem. Abstr. 85: 32558, (1976).

Primary Examiner—Alan L. Rotman
Assistant Examiner—Bernard Dentz

[57] ABSTRACT

4-(((Heterocyclo)thio)methyl)benzoic acids, esters, amides and pharmaceutically-acceptable salts thereof having hypoglycemic activity in mammals, including a method of use and pharmaceutically-acceptable compositions.

42 Claims, No Drawings

4-(((HETEROCYCLO)THIO)METHYL)BENZOIC ACIDS, ESTERS AND AMIDES AND THEIR PHARMACEUTICAL USE

This is a divisional, of application Ser. No. 065,390, filed Aug. 9, 1979, now U.S. Pat. No. 4,325,959.

BACKGROUND OF THE INVENTION

Diabetes mellitus is a disease of mammals which is characterized by an intolerance to carbohydrates and an inadequate production and secretion of insulin by the β-cells in the islets of Langerhans. The disease is often associated with vascular degeneration, especially atherosclerosis. Hypoglycemic agents which are effective in lowering blood sugars may be used in the treatment of certain types of diabetes. U.S. Pat. No. 3,983,164 describes a group of benzoic acid derivatives which have demonstrated hypoglycemic activity.

SUMMARY OF THE INVENTION

The present invention relates to novel 4-(((heterocyclo)thio)methyl)benzoic acid compounds, esters, amides and pharmaceutically-acceptable salts thereof which are active as hypoglycemic agents. The present invention further relates to a method for lowering blood sugar in a mammal using the compounds disclosed herein and to hypoglycemic compositions comprising the active compound in combination with a pharmaceutically-acceptable carrier and other excipients.

Compounds falling within the scope of the present invention may be represented by the general formula

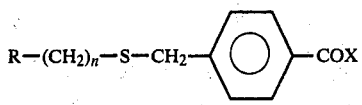

wherein R represents a monocyclic or bicyclic heterocyclic moiety which may be substituted or unsubstituted, said substitution being a lower alkyl or halogen; X represents amino or an —$OR^1$ moiety wherein $R^1$ represents hydrogen or a lower alkyl; and n represents the integer 0, 1, 2 or 3 with the proviso that R is not 5-methyl-2-thiazolyl when n is O and $R^1$ is hydrogen. As used in the specification and claims the term lower alkyl refers to an alkyl having from one to three carbon atoms.

Heterocyclic moieties within the scope of the invention disclosed herein include both monocyclic and bicyclic moieties. Monocyclic moieties showing hypoglycemic activity include pyridinyl; thienyl; thiazolyl; 1,3,4-thiadiazolyl; thiazolinyl; and 1,3,4-oxadiazolyl. Among the substituted monocyclic moieties thiazolyl, thienyl, pyridinyl, 1,3,4-thiadiazolyl and 1,3,4-oxadiazolyl substituted with a lower alkyl, halo or hydroxy are preferred. Bicyclic moieties showing activity include quinolinyl; benzoxazolyl; and benzothiazolyl.

Pharmaceutically-acceptable salts of the 4-(((heterocyclo)thio)methyl)benzoic acid compounds described herein are considered as being within the scope of the invention. Pharmaceutically-acceptable salts refer to the acid addition salts of those bases which will form a salt with the carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like.

The active compounds described above and pharmaceutically-acceptable salts of the compounds when used according to the method of the present invention show hypoglycemic activity in mammals, i.e. lower the level of sugar in the blood. The compounds of the present invention are therefore particularly suitable for use in the treatment of diabetes in mammals characterized by abnormally high levels of glucose in the blood. The compounds can be administered internally to the mammal either orally or parenterally by subcutaneous, intravenous, or intraperitoneal injection or by implantation or the like. Oral administration is generally preferred.

The effective hypoglycemic amount of the active compounds to be internally administered to a mammal, that is the amount which is effective to significantly lower the amount of sugar in the blood, can vary depending upon such factors as the particular benzoic acid derivative, ester, amide, or pharmaceutically-acceptable salt employed, the desired level of blood sugar to be obtained, the severity of the disease, the period of administration, and the method of administration. In general, an effective daily dosage range for the acid and ester compounds of the present invention is from about 2 to about 180 milligrams per kilogram of body weight, with a daily dosage range of from about 15 to about 60 milligrams per kilogram of body weight being preferred. In general, an effective daily dosage range for the amide compounds of the present invention is from about 60 to about 180 milligrams per kilogram of body weight, with a daily dosage range of from about 60 to about 120 milligrams per kilogram of body weight being preferred.

DETAILED DESCRIPTION OF THE INVENTION

One method for preparing the compounds of the present invention is by reacting α-halo-p-toluic acid with a thiol bearing a preselected heterocyclic group in a suitable solvent containing alcohol, generally ethanol, and a suitable scavenger for the halogen, generally sodium hydroxide.

Esters of the compound may be prepared directly from an α-halo-p-toluic acid ester, such as α-bromo-p-toluic acid ester. An equal molar ratio of the α-bromo-p-toluic acid ester and a thiol bearing a preselected heterocyclic group are mixed in a suitable solvent such as toluene and a quantity of triethylamine. The mixture is refluxed, usually for several hours, and then cooled to room temperature. Generally, the reaction mixture is washed with water after which the remaining toluene layer is concentrated in vacuo leaving the desired ester.

To produce the amides, a mixture of the requisite acid and N-hydroxysuccinimide is warmed in a solvent such as acetonitrile until solution is achieved at which point a solution of N,N'-dicyclohexylcarbodiimide in acetonitrile is added; this addition is generally accompanied by the evolution of heat and the formation of a dicyclohexylurea precipitate. After an additional period of reaction the precipitate is removed by filtration and the filtrate concentrated. Trituration with diethyl ether produces the activated ester intermediate. The activated ester is reacted with methanolic ammonia or a solution of methanol saturated with the appropriate substituted amine to give the desired amide.

Pharmaceutically-acceptable salts of the acid may be prepared by treating the free acid with an appropriate base, that is a base which will form a pharmaceutically-acceptable salt with the carboxylic acid and the anions of which are relatively innocuous at dosages consistent with good pharmacological activity so that the desired hypoglycemic properties of the salt are not vitiated by side effects ascribable to the anions.

In carrying out the method of the present invention, the active compound can be administered directly or as an active ingredient of a pharmaceutical preparation or composition. To illustrate, for oral administration, pharmaceutical preparations of the active compounds may be made by following the conventional techniques of the pharmaceutical chemist. These techniques involve granulating and compressing the active compound alone or in admixture with other materials or variously mixing and dissolving or suspending the active compound with other ingredients as appropriate to prepare a predetermined end product. Numerous pharmaceutical forms to carry the compound can be used. For example, the pure compound can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, troches or lozenges and such compositions may be prepared by standard pharmaceutical techniques. Tablet compositions may be coated or uncoated and they may be effervescent or noneffervescent. Conventional excipients for tablet formulations may be used. For example, inert diluents, such as magnesium carbonate, disintegrating agents such as maize starch or alginic acid, and lubricating agents such as magnesium stearate may be used.

If a liquid carrier is used, the preparation may be in the form of a soft gelatin capsule, a syrup, a liquid solution or a suspension.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Especially satisfactory are the pharmaceutically-acceptable glycols, such as propylene glycol, and mixtures thereof. Glycerine is another example of a polyol which is particularly useful. Up to 25-30 percent by volume of water may be incorporated in the vehicle if desired. An 80 percent aqueous propylene glycol solution is a particularly convenient solvent system. A pH range, generally about 7.4, and isotonicity compatible with body isotonicity, is desirable. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

The following examples will serve to further clarify the present invention, but are not to be construed as a limitation thereon.

EXAMPLE 1

Preparation of 4-(((5-methyl-1,3,4-thiadiazol-2-yl)thio)methyl)benzoic acid

A mixture containing 10.75 grams of α-bromo-p-toluic acid (0.05 mole), 6.5 grams of 5-methyl-1,3,4-thiadiazole-2-thiol (0.049 grams), 50 ml of ethanol, 20 ml of 5 N sodium hydroxide, and 150 ml of water was warmed at 50° C. overnight. The clear solution was poured onto 500 ml of ice-water. Upon acidification with concentrated hydrochloric acid the crude product formed as a gelatinous solid. Upon recrystallization 4-(((5-methyl-1,3,4-thiadiazol-2-yl)thio)methyl)benzoic acid was obtained as white crystals having a melting point of 153°-155° C.

Elemental analysis found carbon 49.8%, hydrogen 3.74%, and nitrogen 10.6% as compared to calculated values of carbon 49.6%, hydrogen 3.79%, and nitrogen 10.5%.

EXAMPLE 2

Preparation of 4-((2-pyridinylthio)methyl)benzoic acid

Using the general procedure described above the subject compound was prepared from 16.1 grams (0.075 mole) of α-bromo-p-toluic acid and 8.3 grams (0.075 mole) of 2-mercaptopyridine. The white crystals of 4-((2-pyridinylthio)methyl)benzoic acid had a melting point of 149°-150° C.

Elemental analysis showed carbon 63.7%, hydrogen 4.33%, and nitrogen 5.43% compared to calculated values of carbon 63.7%, hydrogen 4.52% and nitrogen 5.71%.

EXAMPLE 3

Preparation of 4-(((2-(2-thienyl)ethyl)thio)methyl)benzoic acid

A mixture containing 78.2 grams of α-bromo-p-toluic acid (0.363 mole), 27.6 grams of thiourea (0.363 mole) and 500 ml of ethanol was heated to reflux at which point most of the α-bromo-p-toluic acid went into solution. After refluxing for 18 hours, the reaction mixture was cooled and the ethanol solution decanted away from the solid. The ethanol was removed from the ethanol solution in vacuo leaving a portion of the intermediate product as a white solid. The solid remaining in the reaction vessel was recrystallized from water, collected and dried which provided the remaining portion of the intermediate product 4-(((aminoiminomethyl)thio)methyl)benzoic acid monohydrobromide having a melting point of 237°-240° C.

A solution consisting of 24.8 grams of 90% 2-(2-thienyl)-ethanol (0.19 mole) and 250 ml of pyridine was cooled to about 5° C. To the 2-(2-thienyl)-ethanol/pyridine solution was added 72.4 grams of p-toluene sulfonyl chloride (0.38 mole) with the temperature maintained at from 5° to 10° C. When all of the p-toluene sulfonyl chloride had dissolved, the reaction mixture was capped and placed in a refrigerator whereupon white needles of pyridine hydrochloride began to form after approximately fifteen minutes. The mixture was poured over 1 liter of ice-water with the resulting formation of a brown oil.

The oil was extracted from the aqueous mixture by twice extracting with 250 ml of diethyl ether. The diethyl ether solution was washed with 500 ml of 50% HCl and then 500 ml of water. The diethyl ether solution was dried and then concentrated in vacuo to give 4-methylphenyl 2-thiopheneethanesulfonate as a brown oil.

A mixture containing 7.2 grams of 4-(((aminoiminomethyl)thio)methyl)benzoic acid monohydrobromide (0.025 mole), 7.1 grams of 4-methylphenyl 2-thiopheneethanesulfonate (0.025 mole), 50 ml of ethanol, 25 ml of 20% sodium hydroxide in water, and 25 ml of water were warmed to approximately 50° C. The orange solution obtained was mixed with 1 liter of ice-water and acidified with glacial acetic acid giving a pink solid. The pink solid was collected and recrystallized from acetonitrile to give the final product 4-(((2-(2-thienyl)ethyl)thio)methyl)benzoic acid as a pale pink solid having a melting point of 136°-137° C.

Elemental analysis showed carbon 60.7% and hydrogen 5.16% as compared to calculated values of carbon 60.43% and hydrogen 5.07%.

Other benzoic acid compounds falling within the scope of the present invention were prepared in essentially the same manner as already described. These additional compounds, Examples 4-15 inclusive, were as follows.

EXAMPLE 4

4-((((2-chloro-3-thienyl)methyl)thio)methyl)benzoic acid, melting point 119.5°-121° C.

EXAMPLE 5

4-((4-pyridinylthio)methyl)benzoic acid, melting point 268°-270° C.

EXAMPLE 6

4-(((4,5-dihydro-2-thiazolyl)thio)methyl)benzoic acid, melting point 167° C.

EXAMPLE 7

4-((2-benzothiazolylthio)methyl)benzoic acid, melting point 199°-201° C.

EXAMPLE 8

4-((2-quinolinylthio)methyl)benzoic acid, melting point 170°-172° C.

EXAMPLE 9

4-((2-benzoxazolylthio)methyl)benzoic acid, melting point 184°-185° C.

EXAMPLE 10

4-((2-thiazolylthio)methyl)benzoic acid, melting point 133°-134° C.

EXAMPLE 11

4-(((5-methyl-1,3,4-oxadiazol-2-yl)thio)methyl)benzoic acid, melting point 151°-153° C.

EXAMPLE 12

4-(((5-methyl-2-thienyl)thio)methyl)benzoic acid, melting point 148°-151° C.

EXAMPLE 13

4-(((5-chloro-2-pyridinyl)thio)methyl)benzoic acid, melting point 150°-152° C.

EXAMPLE 14

4-(((3-hydroxy-2-pyridinyl)thio)methyl)benzoic acid, melting point 159°-162° C.

EXAMPLE 15

4-((3-pyridinylthio)methyl)benzoic acid, melting point 188°-189° C.

EXAMPLE 16

Preparation of methyl 4-((4-pyridinylthio)methyl)benzoate

A mixture containing 11.0 grams of methyl-p-(bromomethyl)toluate (0.048 mole), 5.3 grams of 4-mercaptopyridine (0.048 mole), 25 ml of triethylamine and 200 ml of toluene was refluxed for 16 hours and then cooled to room temperature. The reaction mixture was washed twice with 300 ml of water. The toluene layer was dried over anhydrous sodium sulfate and then concentrated to give a dark red oil which solidified upon cooling.

After further purification, tan crystals of the product methyl 4-((4-pyridinylthio)methyl)benzoate, confirmed by nuclear magnetic resonance, were obtained having a melting point of 112°-115° C.

EXAMPLE 17

Preparation of ethyl 4-(((5-methyl-1,3,4-thiadiazol-2-yl)thio)methyl)benzoate

A mixture containing 22 grams of ethyl p-(bromomethyl)toluate (0.09 mole), 12 grams of 5-methyl-2-thiol-1,3,4-thiadiazole, 25 ml of triethylamine and 200 ml of toluene were heated to reflux. After 1½ hours the reaction mixture was cooled to room temperature and the triethylamine hydrobromide removed by filtration. The filtrate was concentrated in vacuo to give a brown oil which did not crystallize after overnight drying. The oil was heated to 160° C. for 1 minute and the residue cooled. A small portion of the oil was mixed with hexane in a vial and with scratching crystals formed. The seed crystals were used to crystallize the entire oil. Recrystallization from hexane—toluene (1:1) resulted in yellow crystals of the product ethyl 4-(((5-methyl-1,3,4-thiadiazol-2-yl)thio)methyl)benzoate, confirmed by nuclear magnetic resonance, having a melting point of 55°-58° C.

Other esters falling within the scope of the present invention were prepared in essentially the same manner as previously described herein. These additional esters, Examples 18-20, inclusive, are as follows:

EXAMPLE 18

1-methylethyl 4-(((5-methyl-1,3,4-thiadiazol-2-yl)thio)methyl)benzoate, melting point 66°-70° C.

EXAMPLE 19

Methyl 4-(((5-methyl-1,3,4-thiadiazol-2-yl)thio)methyl)benzoate, melting point 88°-90° C.

EXAMPLE 20

Methyl 4-((2-pyridinylthio)methyl)benzoate, melting point 48°-51° C.

EXAMPLE 21

Preparation of N,N-dimethyl-4-(((5-methyl-1,3,4-thiadiazol-2-yl)thio)methyl)benzamide A mixture of 25 grams of 4-(((5-methyl-1,3,4-thiadiazol-2-yl)thio)methyl)benzoic acid (0.094 mole), 11 grams of 97% N-hydroxysuccinimide (0.094 mole) and 200 ml of acetonitrile was heated until solution was achieved. A solution of 22.7 grams of N,N'-dicyclohexylcarbodiimide (0.11 mole) in 100 ml of acetonitrile was added carefully whereupon the reaction mixture exothermed and a white solid formed. The reaction mixture was stirred at room temperature overnight and then filtered. The filtrate was concentrated and a white solid obtained which was recrystallized from 100 ml of toluene. The white solid obtained upon recrystallization was collected and air-dried leaving the activated ester intermediate 1-((4-(((5-methyl-1,3,4-thiadiazol-2-yl)thio)methyl)benzoyl)oxy)-2,5-pyrrolidinedione having a melting point of 147°–150° C.

A slurry of 3.0 grams of 1-((4-(((5-methyl-1,3,4-thiadiazol-2-yl)thio)methyl)benzoyl)oxy)-2,5-pyrrolidinedione (0.0083 mole) was treated with 50 ml of methanol saturated with dimethylamine. After the mixture of methanol-dimethylamine went into solution, the reaction mixture was concentrated and a viscous oil obtained. Crystals formed upon drying the viscous oil in vacuo. Further purification gave the product N,N-dimethyl-4-(((5-methyl-1,3,4-thiadiazol-2-yl)thio)methyl)benzamide, confirmed by nuclear magnetic resonance, as a white solid having a melting point of 75°–80° C.

Other amides falling within the scope of the present invention were prepared in essentially the same manner as previously described herein. These additional amides, Examples 22 and 23 are as follows:

EXAMPLE 22

4-(((5-methyl-1,3,4-oxadiazol-2-yl)thio)methyl)benzamide, melting point 165°–167+ C.

EXAMPLE 23

4-(((5-methyl-1,3,4-thiadiazol-2-yl)thio)methyl)benzamide, melting point 171°–174° C.

The hypoglycemic activity of the subject compounds may be demonstrated in alanine-induced hyperglycemic mice. Alanine is the most glucogenic of the amino acids and also stimulates gluconeogensis in normal animals. Animals suffering from diabetes show an exaggerated hyperglycemic response to a protein or amino acid meal, therefore the hyperglycemic state induced by alanine closely parallels the response of a diabetic mammal.

The studies were carried out by intraperitoneally injecting fasted male Swiss-Webster mice with various predetermined doses of the active compound. Fifteen minutes later the same mice were injected intraperitoneally with 10 mmoles/kg body weight of L-alanine. Sixty minutes after injection of the active compound, the animals were sacrificed and their sera were analyzed for glucose. The control consisted of both fasted mice and mice injected with alanine only. The results are expressed as percent lowering of serum glucose from the alanine-induced hyperglycemic level to the fasted control glucose level, i.e. lowering to the fasting glucose level is 100% lowering. The results are shown in Table I.

TABLE I

| Compound Example Number | Dosage Level (mg/kg)* | | | |
|---|---|---|---|---|
| | 7.5 | 15 | 30 | 60 |
| 1 | 57 | 106 | 85 | 120 |
| 2 | 116 | 159 | 141 | 140 |
| 3 | 29 | 70 | 95 | 107 |
| 4 | 2 | 7 | 26 | 40 |
| 5 | −5 | 23 | 142 | 181 |
| 6 | −21 | 183 | 174 | 195 |
| 7 | 27 | 2 | 57 | 167 |
| 8 | −62 | −50 | 69 | 150 |
| 9 | 15 | 123 | 136 | 163 |
| 10 | 5 | 26 | 146 | 154 |
| 11 | 3 | 0 | 8 | 129 |
| 12 | — | — | — | 93 |
| 13 | — | — | — | 119 |
| 14 | 18 | 45 | 101 | 169 |
| 15 | 15 | 94 | 129 | 139 |
| 16 | — | — | — | 122 |
| 17 | — | — | — | 125 |
| 18 | — | — | — | 96 |
| 19 | — | — | — | 131 |
| 20 | — | — | — | 122 |
| 21 | — | — | — | 30 |
| 22 | — | — | — | 27 |
| 23 | — | — | — | 27 |

*All figures represent % lowering of serum glucose as compared to controls. Negative numbers represent a % rise in serum glucose.

The data contained in Table I demonstrate the hypoglycemic activity of representative compounds falling within the scope of the present invention. The compound 4-(((5-methyl-1,3,4-thiadiazol-2-yl)-thio)methyl)benzoic acid (Example 1) has been found to have an effective dose ($ED_{50}$) equal to 7.29 mg/kg of body weight, i.e. the dosage at which a 50% lowering of serum glucose is achieved. The compound also has been found to be somewhat less toxic than other compounds of the series, thus resulting in fewer side effects. This compound therefore represents the preferred embodiment of the invention. The other compounds falling within the scope of the present invention although showing slightly higher toxicity or somewhat less hypoglycemic activity than the compound of Example 1 also showed satisfactory hypoglycemic activity in the test animals.

What is claimed is:

1. A compound of the formula:

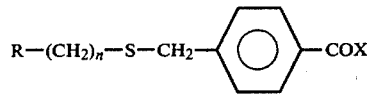

wherein R represents a substituted or unsubstituted heterocyclic moiety selected from the group consisting essentially of pyridinyl, thienyl, and 1,3,4-oxadiazolyl, said optional substitution on the heterocyclic ring being selected from a lower alkyl, halo, or hydroxy; X represents amino or an —$OR^1$ moiety wherein $R^1$ represents hydrogen or lower alkyl; and n represents the integer 0, 1, 2 or 3 or a pharmaceutically-acceptable salt of the acid.

2. The compound of claim 1 which is 4-((2-pyridinylthio)methyl)benzoic acid or a pharmaceutically-acceptable salt thereof.

3. The compound of claim 1 which is 4-(((2-(2-thienyl)ethyl)thio)methyl)benzoic acid or a pharmaceutically-acceptable salt thereof.

4. The compound of claim 1 which is 4-((((2-chloro-3-thienyl)methyl)thio)methyl)benzoic acid or a pharmaceutically-acceptable salt thereof.

5. The compound of claim 1 which is 4-((4-pyridinylthio)methyl)benzoic acid or a pharmaceutically-acceptable salt thereof.

6. The compound of claim 1 which is 4-(((5-methyl-1,3,4-oxadiazol-2-yl)thio)methyl)benzoic acid or a pharmaceutically-acceptable salt thereof.

7. The compound of claim 1 which is 4-(((5-methyl-2-thienyl)thio)methyl)benzoic acid or a pharmaceutically-acceptable salt thereof.

8. The compound of claim 1 which is 4-(((5-chloro-2-pyridinyl)thio)methyl)benzoic acid or a pharmaceutically-acceptable salt thereof.

9. The compound of claim 1 which is 4-(((3-hydroxy-2-pyridinyl)thio)methyl)benzoic acid or a pharmaceutically-acceptable salt thereof.

10. The compound of claim 1 which is 4-((3-pyridinylthio)methyl)benzoic acid or a pharmaceutically-acceptable salt thereof.

11. The compound of claim 1 which is methyl 4-((4-pyridinylthio)methyl)benzoate.

12. The compound of claim 1 which is methyl 4-((2-pyridinylthio)methyl)benzoate.

13. The compound of claim 1 which is 4-(((5-methyl-1,3,4-oxadiazol-2-yl)thio)methyl)benzamide.

14. A method for treating hyperglycemia in a mammal which comprises administering internally to a mammal an effective hypoglycemic amount of a compound of the formula:

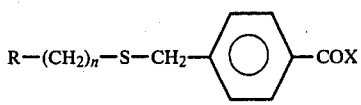

wherein R represents a substituted or unsubstituted heterocyclic moiety selected from the group consisting essentially of pyridinyl, thienyl, and 1,3,4-oxadiazolyl, said optional substitution on the heterocyclic ring being selected from a lower alkyl, halo, or hydroxy; X represents amino or an —$OR^1$ moiety wherein $R^1$ represents hydrogen or lower alkyl; and n represents the integer 0, 1, 2 or 3 or a pharmaceutically-acceptable salt of the acid.

15. The method of claim 14 wherein R of the compound is pyridinyl.

16. The method of claim 14 wherein the effective hypoglycemic amount of the compound when X is —$OR^1$, is a daily dosage of 15 to 60 milligrams per kilogram of body weight.

17. The method of claim 14 wherein the effective hypoglycemic amount of the compound when X is amino, is a daily dosage of 60 to 120 milligrams per kilogram of body weight.

18. The method of claim 14 wherein the compound is 4-((2-pyridinylthio)methyl)benzoic acid or a pharmaceutically-acceptable salt thereof.

19. The method of claim 14 wherein the compound is 4-(((2-(2-thienyl)ethyl)thio)methyl)benzoic acid or a pharmaceutically-acceptable salt thereof.

20. The method of claim 14 wherein the compound is 4-((((2-chloro-3-thienyl)methyl)thio)methyl)benzoic acid or a pharmaceutically-acceptable salt thereof.

21. The method of claim 14 wherein the compound is 4-((4-pyridinylthio)methyl)benzoic acid or a pharmaceutically-acceptable salt thereof.

22. The method of claim 14 wherein the compound is 4-(((5-methyl-1,3,4-oxadiazol-2-yl)thio)methyl)benzoic acid or a pharmaceutically-acceptable salt thereof.

23. The method of claim 14 wherein the compound is 4-(((5-methyl-2-thienyl)thio)methyl)benzoic acid or a pharmaceutically-acceptable salt thereof.

24. The method of claim 14 wherein the compound is 4-(((5-chloro-2-pyridinyl)thio)methyl)benzoic acid or a pharmaceutically-acceptable salt thereof.

25. The method of claim 14 wherein the compound is 4-(((3-hydroxy-2-pyridinyl)thio)methyl)benzoic acid or a pharmaceutically-acceptable salt thereof.

26. The method of claim 14 wherein the compound is 4-((3-pyridinylthio)methyl)benzoic acid or a pharmaceutically-acceptable salt thereof.

27. The method of claim 14 wherein the compound is methyl 4-((4-pyridinylthio)methyl)benzoate.

28. The method of claim 14 wherein the compound is methyl 4-((2-pyridinylthio)methyl)benzoate.

29. The method of claim 14 wherein the compound is 4-(((5-methyl-1,3,4-oxadiazol-2-yl)thio)methyl)benzamide.

30. A composition for the treatment of hyperglycemia in a mammal comprising a pharmaceutically-acceptable carrier in combination with an effective hypoglycemic amount of a compound having the formula:

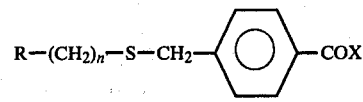

wherein R represents a substituted or unsubstituted heterocyclic moiety selected from the group consisting essentially of pyridinyl, thienyl, and 1,3,4-oxadiazolyl, said optional substitution on the heterocyclic ring being selected from a lower alkyl, halo, or hydroxy; X represents amino or an —$OR^1$ moiety wherein $R^1$ represents hydrogen or lower alkyl; and n represents the integer 0, 1, 2 or 3 or a pharmaceutically-acceptable salt of the acid.

31. The composition of claim 30 wherein the compound is 4-((2-pyridinylthio)methyl)benzoic acid or a pharmaceutically-acceptable salt thereof.

32. The composition of claim 30 wherein the compound is 4-(((2-(2-thienyl)ethyl)thio)methyl) benzoic acid or a pharmaceutically-acceptable salt thereof.

33. The composition of claim 30 wherein the compund is 4-((((2-chloro-3-thienyl)methyl)thio)methyl)benzoic acid or a pharmaceutically-acceptable salt thereof.

34. The composition of claim 30 wherein the compound is 4-((4-pyridinylthio)methyl)benzoic acid or a pharmaceutically-acceptable salt thereof.

35. The composition of claim 30 wherein the compound is 4-(((5-methyl-1,3,4-oxadiazol-2-yl)thio)methyl)benzoic acid or a pharmaceutically-acceptable salt thereof.

36. The composition of claim 30 wherein the compound is 4-(((5-methyl-2-thienyl)thio)methyl)benzoic acid or a pharmaceutically-acceptable salt thereof.

37. The composition of claim 30 wherein the compound is 4-(((5-chloro-2-pyridinyl)thio)methyl)benzoic acid or a pharmaceutically-acceptable salt thereof.

38. The composition of claim 30 wherein the compound is 4-(((3-hydroxy-2-pyridinyl)thio)methyl)benzoic acid or a pharmaceutically-acceptable salt thereof.

39. The composition of claim 30 wherein the compound is 4-((3-pyridinylthio)methyl)benzoic acid or a pharmaceutically-acceptable salt thereof.

40. The composition of claim 30 wherein the compound is methyl 4-((4-pyridinylthio)methyl)benzoate.

41. The composition of claim 30 wherein the compound is methyl 4-((2-pyridinylthio)methyl)benzoate.

42. The composition of claim 30 wherein the compound is 4-(((5-methyl-1,3,4-oxadiazol-2-yl)thio)methyl)benzamide.

* * * * *